United States Patent [19]
Gojon-Zorrilla et al.

[11] Patent Number: 5,329,027
[45] Date of Patent: Jul. 12, 1994

[54] OXIDATIVE DEHALOGENATION PROCESS FOR THE PRODUCTION OF PERCHLORINATED QUINONES

[75] Inventors: Gabriel Gojon-Zorrilla, Nuevo Leon; Ignacio Villanueva-Fierro, Mexicali; Antonio Hinojosa-Martinez, Monterrey, all of Mexico

[73] Assignee: Grupo Cydsa, S.A. de C.V., Nuevo Leon, Mexico

[21] Appl. No.: 980,405

[22] Filed: Nov. 24, 1992

[51] Int. Cl.$^5$ .............................................. C07C 50/24
[52] U.S. Cl. ................................................... 552/308
[58] Field of Search ......................................... 552/308

[56] References Cited

U.S. PATENT DOCUMENTS

| | | | |
|---|---|---|---|
| 2,414,008 | 1/1947 | Alquist et al. | 552/308 |
| 2,422,089 | 6/1947 | Fletcher | 552/308 |
| 2,422,229 | 6/1947 | Fletcher | 552/308 |
| 2,975,196 | 3/1961 | Sjostrand | 260/396 |
| 3,728,561 | 4/1973 | Fuhlhage | 260/396 R |
| 3,873,580 | 3/1975 | Rennie | 260/362 |
| 3,897,464 | 7/1975 | Dohm | 260/346.4 |
| 4,032,548 | 6/1977 | Martin | 260/396 R |
| 4,196,132 | 4/1980 | Bader | 260/396 R |
| 4,519,948 | 5/1985 | Hsu et al. | 552/308 |
| 5,075,462 | 12/1991 | Kuo et al. | 552/308 |
| 5,075,463 | 12/1991 | Kuo et al. | 552/299 |
| 5,149,850 | 9/1992 | Arndt et al. | 552/308 |
| 5,151,532 | 9/1992 | Arndt et al. | 552/308 |

*Primary Examiner*—Paul J. Killos
*Attorney, Agent, or Firm*—Shlesinger, Arkwright & Garvey

[57] ABSTRACT

The present invention relates to an improved process for the production of perchlorinated quinones by oxidative dehalogenation comprising the steps of providing a stoichiometric mixture consisting of sulfur trioxide, sulfuric acid and at least one aromatic compound containing one or more unsaturated carbon-rings therein. The mixture is reacted with a stoichiometric quantity of chlorine by slowly adding the chlorine to the mixture while stirring. After a sufficient reaction time the resultant perchlorinated quinone product is recovered from the reacted mixture.

13 Claims, 1 Drawing Sheet

OXIDATIVE DEHALOGENATION PROCESS FOR THE PRODUCTION OF PERCHLORINATED QUINONES

FIELD OF INVENTION

The present invention relates to a process for the production of perchlorinated quinones from a perhalogenated aromatic substrate via oxidative dehalogenation and more specifically to the production of tetrachloro-p-benzoquinone (chloranil).

BACKGROUND OF THE INVENTION

Perchlorinated quinones are well known in the art providing a variety of uses in both the chemical and pharmaceutical industries. For example, chloranil (2, 3, 5, 6-tetrachloro-p-benzoquinone) is a powerful oxidant which has been used in the oxidation and dehydrogenation of a large number of organic compounds. It is used commercially as an oxidizing agent in the preparation of dyes such as methyl violet and as a fungicide in agricultural applications. Chloranil is also known to be a useful reagent for tamaquine detection in urine.

Various industrial processes exist for the manufacture of chloranil. U.S. Pat. No. 2,722,537 (Fox) discloses a process for the preparation of chloranil through oxidative chlorination of cyclohexane using hydrogen chloride and oxygen at a temperature between 180° and 260° C. U.S. Pat. No. 2,414,008 (Alquist et. al.) discloses the production of chloranil by admixing a polychlorophenol with concentrated sulfuric acid and passing chlorine into the heated mixture. U.S. Pat. No. 2,422,229 (Fletcher) discloses a process for manufacturing chlorinated quinones by chlorination of derivatives of phenol and alphahydroxynapthalene, the derivatives being present in a liquid medium comprising a mixture of sulfuric acid and acetic acid.

Although the above noted prior art processes do in fact produce chloranil, they often suffer from low yields and exist as relatively "dirty" reactions generating excessive and unwanted byproducts.

OBJECTS AND SUMMARY OF THE INVENTION

The present invention relates to an improved process for the production of perhalogenated quinones by oxidative dehalogenation comprising the steps of providing a stoichiometric mixture consisting of sulfuric acid, sulfur trioxide and a substrate starting material comprising at least one aromatic compound containing one or more unsaturated carbon-rings therein. A catalytic amount of elemental iodine is added and the mixture is reacted with a quantity of chlorine by slowly adding the chlorine to the mixture while stirring. After a sufficient reaction time the resultant perhalogenated quinone product is recovered from the reacted mixture.

It is an object of the present invention to provide a process for the production of perchlorinated quinones where the precursor perchloroaromatic compounds capable of being oxidatively dehalogenated are produced "in situ" within the reaction vessel.

Yet a further object of the present invention is to provide an method for the production of perchlorinated quinones which may be carried out at a wide variety of reaction temperatures and conditions.

A still further object of the present invention is to provide a reaction for the production of perchlorinated quinones by a oxidative dehalogenation reaction which may be carried out at either superatmospheric pressure, atmospheric pressure or in vacuum.

Another object of the present invention is to provide an oxidative dehalogenation process employing either pure chlorine gas or chlorine gas in combination with other inert gases.

A still further object of the present invention is to provide a process for the production of perchlorinated quinones which is commercially economical and results in a higher and more pure yield of chloranil.

Yet another object of the present invention is to provide a process for the production of chloranil which contains virtually no unwanted byproducts.

The manner in which these as well as other objects of the present invention can be accomplished will be apparent from the following detailed description and examples.

DETAILED DESCRIPTION OF THE PREFERRED EMBODIMENT

Figure 1:
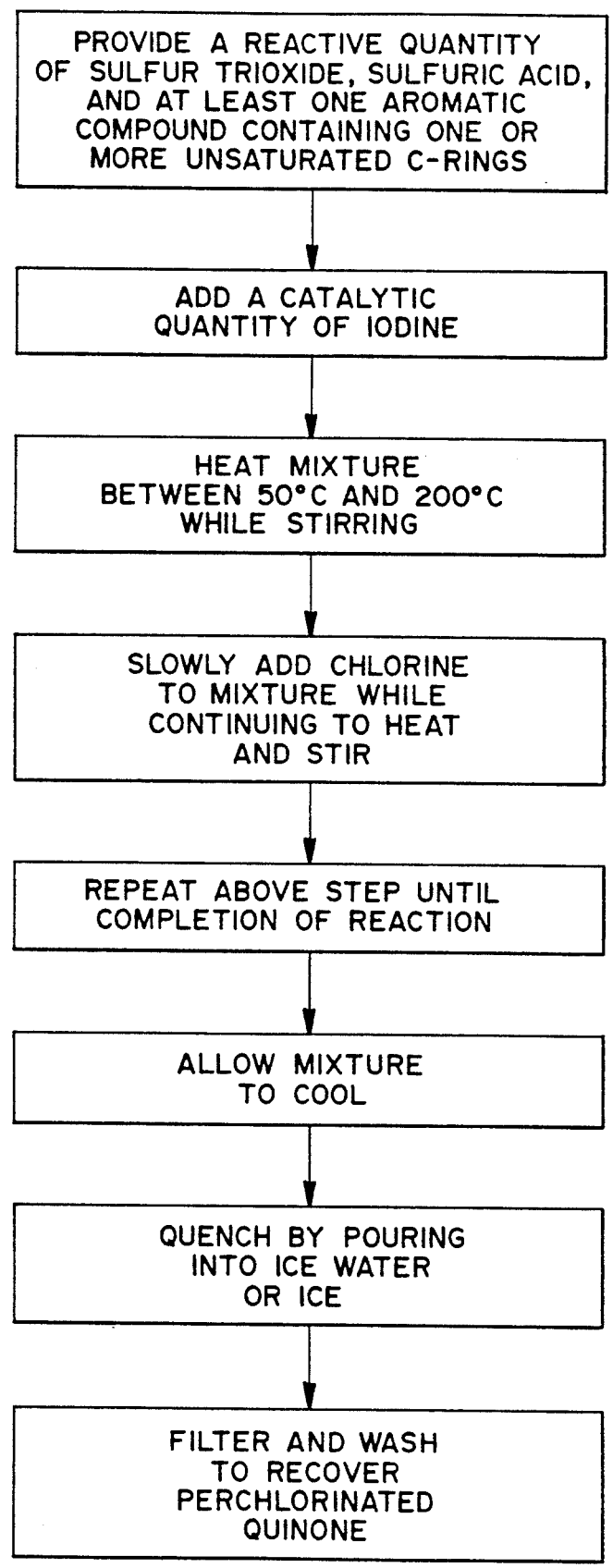
FIG. 1 is a schematic diagram illustrating the steps in the process for the production of perchlorinated quinones according to the present invention.

The process according to present invention is the oxidative dehalogenation of perhalogenated aromatic compounds. Applicants have discovered that an improved oxidative dehalogenation process for the production of perchlorinated quinones is now possible. Referring to FIG. 1, a starting mixture is provided containing a stoichiometric quantity of at least one aromatic compound having one or more unsaturated carbon-rings therein, sulfuric acid and a sulfur trioxide compound. A catalytic proportion of iodine is then added to the reactive mixture. The mixture is heated to a temperature between 50° C. and 200° C. and constantly stirred while pure chlorine gas or chlorine gas in admixture with inert gases is slowly bubbled through the mixture. The chlorine gas flow step is continued until most of the substrate starting material is exhausted at which time the flow is interrupted and the now reacted mixture is permitted to cool followed by separation of the chloranil end product.

Applicants have found that this combination chlorine-iodine-fuming sulfuric acid mixture constitutes a powerful chlorinating system capable of replacing with chlorine atoms all of the hydrogen atoms from the ring and side chains of the aromatic and alkaromatic organic substrate compound as well as causing carbon-carbon and carbon-heteroatom bond cleavage through chlorinolysis. This reaction is particularly suitable for the production of tetrachloro-p-benzoquinone from any of a wide variety of precursor compounds which produce the perchlorobenzene substrate in situ. For example, pentachloronitrobenzene as a starting material is capable of yielding a perchlorinated substrate of perchlorobenzene according to the method of the present invention. This perchlorobenzene substrate is then dehalogenated according to the present process to produce the chloranil perchlorinated quinone.

Precursor starting materials within the scope of the present invention include a variety of aromatic derivatives which when reacted yield the perchlorinated substrate required for the production of the end product perchlorinated quinones. Applicants have found that suitable starting materials include benzene, biphenyl, diphenylmethane and alkyl, cycloalkyl, substituted alkyl, substituted cycloalkyl, chloro, bromo, iodo, nitro, hydroxy, alkoxy, acyloxy, aryloxy, amino, substituted amino, cyano, carboxy, carboalkoxy, carboaryloxy, acyl, carboxamide, substituted carboxamide, sulfamide and substituted sulfamide derivatives as well as other derivatives containing heteroatoms directly attached to the aromatic nuclei. For example, sulfonic acids, arylphosphonic acids, quaternary ammonium salts, quaternary phosphonium salts, sulphonium salts, triaryl phosphates and phosphites are all within the scope of the present invention. Other suitable starting materials are contemplated within the scope of the present invention so long as such materials are capable of generating the required perchlorinated substrates "in situ".

A preferred sulfur trioxide component starting material according to the present invention is fuming sulfuric acid commercially known as oleum. Fuming sulfuric acid is available in various grades containing up to about 80% free sulfur trioxide. Sulfur trioxide may also be combined with sulfuric acid and chlorosulfuric acid for use according to the present invention. Applicants have found that the sulfur trioxide is generally added in amounts in excess of the stoichiometric quantities since fuming sulfuric acid also acts as a solvent. Additional solvents may be added to the mixture along with the sulfur trioxide. For example, acetic acid or acid anhydride, two essentially inert solvents may be used as additives.

Suitable catalysts according to the present invention include iodine, iodine monochloride and iodine trichloride. Other iodine-type catalysts are contemplated within the scope of the present invention. Since iodine and chlorine are known to react under the reaction conditions, applicants theorize that it is very likely the actual catalyst is not iodine but iodine monochloride and/or iodine trichloride.

Applicants have found that the process according to the present invention can be carried out with flexibility and within a variety of parameters. Chlorine gas may be provided either in elemental form or in admixture with inert gases and is also added in quantities in excess of the stoichiometric requirements since it is continuously bubbled through the mixture as the reaction proceeds. Chlorine may also be supplied in the form of phosphorous pentachloride, antimony pentachloride, sulfuryl chloride or sulfuryl chlorofluoride. The chlorine gas is slowly passed through the mixture containing the sulfur trioxide, sulfuric acid, organic substrate and iodine catalyst. Chlorine addition is generally terminated between one and four hours, however as noted above, chlorine may continue to be added beyond that time frame so long as some substrate material remains to be dehalogenated.

The reaction according to the present invention can be effectively carried out at a temperature selected between about 50° C. to 200° C. but a preferred temperature range extends between 80° C. and 150° C. Super atmospheric pressure is not required but it may be advantageous to carry out the process above atmospheric pressure if higher reaction temperatures are used so as to prevent the loss of sulfur trioxide from the reaction mixture. The reaction can also be carried out at atmospheric pressure or in vacuum if so desired.

The invention is further illustrated by, but not limited to, the following examples:

EXAMPLE 1

Chlorine (22 g.; 0.31 mole) was passed slowly (1 hour) into a mechanically stirred (150 r.p.m.) mixture containing 300 ml (400 g.) of fuming sulfuric acid (20% sulfur trioxide), 0.2 g. (0.00078 mole) of iodine and 10.0 g (0.035 mole) of hexachlorobenzene (HCB). The reaction mixture temperature maintained at 1100° C. The reaction may be illustrated by the following equation:

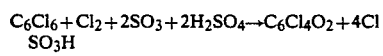

Once the chlorine flow was interrupted, it was all0wed to cool to room temperature and slowly and carefully poured without stirring into a large mass of ice. The resultant solid was separated by filtration, washed with distilled water, rewashed with a dilute aqueous sodium bicarbonate solution and again washed with distilled water followed by drying. The bright yellow colored end product (7.8 g.) contained 98.1% chloranil (89% yield). This end product was analyzed by gas chromatography using a 10% DC-200 chromosorb G/AW-DMCS treated column (180° C.) installed in a VARIAN ® 3700 gas chromatograph coupled with a VARIAN ® SP4270 Integrator-Recorder. The crude product was recrystallized from acetone to yield pure chloranil having a melting point of 286°-287° C. This crude product also contained small amounts of unreacted hexachlorobenzene (1.9% w/w).

EXAMPLE 2

Chlorine (66 g.; 0.93 mole) was passed slowly (3 hours) into a mechanically stirred (500 r.p.m.) mixture containing 800 g. (440 ml.) of fuming sulfuric acid (20% sulfur trioxide) and 50 g. (0.175 mole) of hexachlorobenzene. The reaction mixture temperature was maintained at 100° C.; when the chlorine flow was interrupted it was allowed to cool to room temperature and then worked up under the same procedure as given under Example 1. The solid product was analyzed by gas chromatograph and iodometry; it was found to contain 9.01% (w/w) chloranil (10% yield based on the hexachlorobenzene charged into the reactor) and 91% hexachlorobenzene.

EXAMPLE 3

Chlorine (66.7 g.; 0.94 mole) was passed slowly (3 hours) into a mechanically stirred (150 r.p.m.) mixture comprising 300 ml of fuming sulfuric acid (20% sulfur trioxide), 0.2 g. (0.00078 mole) of iodine and 20.0 g. (0.068 mole) of pentachloronitrobenzene. The reaction mixture temperature was maintained at 110°C.; when the chlorine flow was interrupted it was allowed to cool and then worked up as given under Example 1. The crude product (12.9 g. ) contained 96.5% (w/w) chloranil by gas chromatograph analysis (76% yield); it also contained 1.9% (w/w) unreacted pentachloronitrobenzene.

EXAMPLE 4

Chlorine (53.2 g.; 0.75 mole) was passed slowly (3 hours) into a mechanically stirred (500 r.p.m.) mixture comprising 147 ml. of fuming sulfuric acid (20% sulfur trioxide), 0.1 g. (0.00039 mole) of iodine and 15.6 g. (0.0586 mole) of pentachlorophenol. The reaction mixture temperature was maintained at 100° C. The reaction may be illustrated by the following:

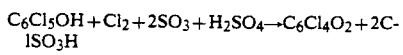

When the chlorine flow was interrupted it was allowed to cool to room temperature and then worked up as given under Example 1. The crude product contained 97% (w/w) chloranil by gas chromatograph analysis, its yield amounted to 95% of theory.

EXAMPLE 5

Chlorine (179.6 g.; 2.53 mole) was passed slowly (4 hours) into a mechanically stirred (400 r.p.m.) mixture comprising 420 ml. of fuming sulfuric acid (20% sulfur trioxide), 0.2 g. (0.00078 mole) iodine, 103 millimoles of tetrachloronitrobenzene isomers and 78 millimoles pentachloronitrobenzene. The reaction mixture temperature maintained at 100° C.; when the chlorine flow was interrupted, the mixture was allowed to cool to room temperature and then worked up as detailed under Example 1. The crude product contained 116 millimoles of chloranil, 0.5 millimoles pentachloronitrobenzene and 0.07 millimoles hexachlorobenzene by gas chromatograph analysis.

EXAMPLE 6

Chlorine (66 g.; 0.93 mole) was passed slowly (3 hours) into a mechanically stirred (500 r.p.m.) mixture comprising 220 ml. of oleum (20% sulfur trioxide), 0.15 g. (0.00058 mole) iodine and 14.89 g. (0.0875 mole) diphenyl ether. The reaction mixture temperature was maintained at 100° C. The reaction may be illustrated by the following equation:

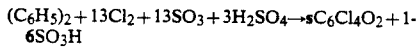

When the chlorine flow as interrupted, the mixture was allowed to cool to room temperature and then worked up as detailed under Example 1. The crude product (10 g.) contained chloranil (99.73% purity by gas chromatograph analysis); elemental analysis by Galbraith Laboratories gave 29.32% total carbon and 57.38% total chlorine content.

EXAMPLE 7

Chlorine (66 g.; 0.93 mole) was passed slowly (3 hours) into a mechanically stirred (500 r.p.m.) mixture comprising 200 g. (110 ml.) of oleum (20% sulfur trioxide), 0.075 g. (0.000591 mole) iodine and 24.208 g. (0.04389 mole) hexabromobenzene. The reaction mixture temperature was maintained at 100° C.; when the chlorine flow was interrupted, the mixture was allowed to cool to room temperature and then worked up as detailed under Example 1. The crude product (11 g.) was analyzed by gas chromatography and found to contain chloranil and hexachlorobenzene. The chloranil peak had an area that amounted to 44.76% of the area of all peaks.

EXAMPLE 8

Chlorine (44 g.; 0.62 mole) was passed slowly (2 hours) into a mechanically stirred (500 r.p.m.) mixture comprising 100 g. (55 ml.) oleum (20% sulfur trioxide), 0.0375 g. (0.00015 mole) iodine and 18.3 g. (0.022 mole) hexaiodobenzene. The reaction mixture temperature was maintained at 1000° C.; when the chlorine flow was interrupted, the mixture was allowed to cool to room temperature and then worked up as detailed under Example 1. The crude product (4.0 g.) was found to contain 1.52 g. chloranil (29.08% yield) and 1.01 g. hexachlorobenzene by gas chromatography.

The stoichiometric requirements for the reaction set forth in Example 1 indicate that for each mole of $C_6Cl_6$ (285 g.), one mole of chlorine (71 g.) and two moles of $SO_3$ (160 g.) are required. Since $SO_3$ is added via oleum containing 20% $SO_3$, 800 g. of oleum are required. Applicants have found however that because the chlorine is bubbled through the reaction mixture, it must be added in great excess. For example, although 8.85 moles of chlorine were added per mole of HCB in Example 1, most of the chlorine passes through the reaction mixture without undergoing reaction.

Similarly, sulfur trioxide must be present in great excess. In Example 1, the fuming sulfuric acid contains 20% $SO_3$ and has a density of 1.82 and 300 ml. were used, therefore:

| | | |
|---|---|---|
| 300 ml. × 1.82 g/ml | = 546 g. | |
| $SO_3$ content | = 546 × 0.2 g. | = 109.2 g. |
| | = 109.2 g/80 g. per mole | = 1.37 mole |

Thus, 30 moles of $SO_3$ were added per single mole of HCB in Example 1. Applicants theorize that excessive quantities of fuming sulfuric acid are required since it also functions as a solvent. Further, since $SO_3$ is known to react with HCl and form chlorosulfuric acid ($SO_3 + HCl \rightarrow Cl\ SO_3H$), each mole of byproduct HCl formed during the reaction (if a hydrogen containing unsaturated C-ring starting compound is used) might react with one mole of $SO_3$. This increased stoichiometric requirement for $SO_3$/fuming sulfuric acid is most apparent in Examples 5 and 6.

The following Table 1 illustrates the variable theoretical stoichiometric requirements of $Cl_2$ per mole of substrate:

TABLE 1

| Example | moles $Cl_2$/required per single mole of substrate |
|---|---|
| 1 | 1 |
| 3 | 2 |
| 4 | 2 |
| 5 | — |
| 6 | 14 |
| 7 | 7 |
| 8 | 7 |

Since a mixture of substrates was used in Example 5, two extra moles of $Cl_2$ are required per mole of tetrachloronitrobenzene (TCNB) and one extra mole of $Cl_2$ per mole of pentachloronitro-benzene (PCNB) are required. Because the initial reaction mixture contained 0.103 moles TCNB (26.8 g.) and 0.078 mole PCNB (23 g.), 0.284 extra moles (2×0.113+0.078=0.1284) of $Cl_2$ are required.

In most of the examples, only two moles of $SO_3$ would be required per mole of substrate except in the case of Example 6 where thirteen moles are required and in the case of example 3 where three moles are required. Further, Applicants theorize that in the cases of pentachlorophenol (Example 4) and diphenyl ether (Example 6) the reaction may in fact not proceed through HCB through completion and one less moles of $Cl_2$ would be required than the amounts set forth in Table 1.

While the invention has been disclosed as having a preferred design, it is understood that it is capable of further modifications, uses and/or adaptations of the invention following in general the principle of the invention and including such departures from the present disclosure as come within known or customary practice in the art to which the invention pertains, and as may be applied to the central features hereinbefore set forth, and fall within the scope of the invention of the limits of the appended claims.

What is claimed is:

1. An improved process for the production of perchlorinated quinones by oxidative dehalogenation comprising the steps of:
   a) providing a stoichiometric mixture consisting of sulfur trioxide, sulfuric acid and at least one aromatic compound containing one or more unsaturated carbon-rings therein;
   b) reacting with the mixture at least a stoichiometric quantity of chlorine by slowly adding the chlorine to the mixture; and
   c) recovering the produced perchlorinated quinone from the reacted mixture.

2. The process as in claim 1 and wherein:
   a) the mixture is reacted in the presence of a catalyst.

3. The process as in claim 1 and wherein:
   a) the catalyst is selected from the group consisting of iodine, iodine monochloride and iodine trichloride.

4. The process as in claim 1 and including the step of:
   a) stirring the mixture while adding the chlorine.

5. The process as in claim 1 and wherein:
   a) the reaction is carried out at a temperature greater than 50° C. during addition of the chlorine.

6. The process as in claim 5 and including the step of:
   a) allowing the mixture to cool to room temperature after addition of the chlorine.

7. The process as in claim 6 and including the step of:
   a) pouring the cooled mixture into an ice bath, ice water or ice to yield a solid mass containing the perchlorinated quinone.

8. The process as in claim 1 and wherein:
   a) the reaction is carried out at a pressure selected from the group consisting of atmospheric pressure, super atmospheric pressure and in vacuum.

9. The process as in claim 1 and wherein:
   a) the chlorine is elemental chlorine gas in pure form or in admixture with inert gases.

10. The process as in claim 1 and wherein:
    a) the chlorine is replaced by a chlorine carrier selected from the group consisting of phosphorous pentachloride and antimony pentachloride.

11. The process as in claim 7 and including the steps of:
    a) filtering the solid mass from the aqueous phase;
    b) washing the filtered solid with water;
    c) rewashing the filtered solid with a dilute aqueous sodium bicarbonate solution;
    d) rewashing the filtered solid with water and
    e) drying the solid to recover the perchlorinated quinone.

12. The process as in claim 1 and wherein:
    a) the recovered perchlorinated quinone is chloranil.

13. The process as in claim 1 and further comprising the step of:
    a) including within the stoichiometric mixture a chlorosulfuric acid.

* * * * *